United States Patent [19]

Lewis et al.

[11] 4,289,634

[45] Sep. 15, 1981

[54] DEPOSIT CONTROL ADDITIVES AND FUEL AND LUBE OIL COMPOSITIONS CONTAINING THEM

[75] Inventors: Robert A. Lewis, Berkeley; Lewis R. Honnen, Petaluma, both of Calif.

[73] Assignee: Chevron Research Company, San Francisco, Calif.

[21] Appl. No.: 60,307

[22] Filed: Jul. 25, 1979

[51] Int. Cl.³ .................. C10M 1/46; C10M 1/32; C10M 3/40; C10L 1/26

[52] U.S. Cl. .................. 252/32.5; 44/71; 44/76; 252/389 A; 260/924; 260/925

[58] Field of Search ............ 252/32.5, 389 A; 44/71, 44/76; 260/924, 925

[56] References Cited

U.S. PATENT DOCUMENTS

| | | | |
|---|---|---|---|
| 3,775,446 | 11/1973 | Weghoff et al. | 260/925 |
| 3,962,104 | 6/1976 | Swietlik et al. | 252/34 |
| 3,969,237 | 7/1976 | Andress | 252/32.5 |
| 3,996,024 | 12/1976 | Coon et al. | 44/71 |
| 4,160,648 | 7/1979 | Lewis et al. | 44/71 |
| 4,177,768 | 12/1979 | Davis | 44/66 |
| 4,197,409 | 4/1980 | Lilburn | 44/71 |
| 4,198,306 | 4/1980 | Lewis | 44/71 |
| 4,233,168 | 11/1980 | Lewis et al. | 252/51.5 A |
| 4,236,020 | 11/1980 | Lewis et al. | 44/71 |

*Primary Examiner*—Delbert E. Gantz
*Assistant Examiner*—Irving Vaughn
*Attorney, Agent, or Firm*—D. A. Newell; A. S. Zavell

[57] ABSTRACT

Combination deposit and rust control additives for internal combustion engines are provided which maintain cleanliness of intake systems without contributing to combustion chamber deposits and corrosion. The additives are salts of hydrocarbyl oxyacid esters of phosphorus and of hydrocarbylpoly(oxyalkylene) aminocarbamates comprising a hydrocarbyl-terminated poly(oxyalkylene) chain of 2-5 carbon oxyalkylene units bonded through an oxycarbonyl group to a nitrogen atom of a polyamine. Lube oil and fuel compositions containing these additive salts are also provided for use in internal combustion engines.

11 Claims, No Drawings

DEPOSIT CONTROL ADDITIVES AND FUEL AND LUBE OIL COMPOSITIONS CONTAINING THEM

BACKGROUND OF THE INVENTION

1. Field of the Invention

In recent years, numerous fuel and lube oil detergents or "deposit control" additives have been developed. These materials when added to hydrocarbon fuels and lube oils employed in internal combustion engines effectively reduce deposit formation which ordinarily occurs in carburetor ports, throttle bodies, ventures, intake ports and intake valves and other ports of the engines. The reduction of these deposit levels has resulted in increased engine efficiency and a reduction in the level of hydrocarbon and carbon monoxide emissions.

Thus, the introduction of fuel compositions containing deposit control additives has resulted in many cases in the reduction of harmful atmospheric pollutants and, since greater engine efficiencies are maintained; fuel savings.

A complicating factor has, however, recently arisen. With the advent of automobile engines that require the use of non-leased gasolines (to prevent disablement of catalytic converters used to reduce emissions), it has been difficult to provide gasoline of high enough octane to prevent knocking and the concomitant damage which it causes. The chief problem lies in octane requirement increase, herein called "ORI", which is caused by deposits formed in the combustion chamber while the engine is operating on commercial gasoline.

The basis of the ORI problem is as follows: each engine, when new, requires a certain minimum octane fuel in order to operate satisfactorily without pinging and/or knocking. As the engine is operated on any gasoline, this minimum octane increases and, in most cases, if the engine is operated on the same fuel for a prolonged period, will reach equilibrium. This is apparently caused by an amount of deposits in the combustion chamber. Equilibrium is typically reached after 5000 to 15,000 miles of automobile operation.

Octane requirement increase, measured in particular engines with commercial gasolines, will vary at equilibrium from 5 or 6 octane units to as high as 12 or 15 units, depending upon the gasoline compositions, engine design and type of operation. The seriousness of the problem is thus apparent. A typical 1975 or 1976 automobile with a research octane requirement of 85 when new may after a few months of operation require 97 research octane gasoline for proper operation, and little unleaded gasoline of that octane is available. The ORI problem exists in some degree with engines operated on leaded fuels. U.S. Pat. Nos. 3,144,311 and 3,146,203 disclose lead-containing fuel compositions having reduced ORI properties.

It is believed, however, by many experts that the ORI problem, while present with leaded gasolines, is much more serious with unleaded fuel because of the different nature of the deposits formed with the respective fuels, the size of increase, and because of the lesser availability of high-octane non-leaded fuels. This problem is compounded by the fact that the most common means of enhancing the octane of unleaded gasoline, increasing its aromatic content, also appears to increase the eventual octane requirement of the engine. Furthermore, some of the presently used nitrogen-containing deposit control additives and the mineral oil or polymer carriers commonly used with such additives appear to contribute significantly to the ORI of engines operated on unleaded fuel.

It is, therefore, highly desirable to provide deposit control additives which effectively control deposits in intake systems (carburetor, valves, etc.) of engines operated with fuels containing them, but do not contribute to the combustion chamber deposits which cause increased octane requirements.

In our pending allowed application U.S. Ser. No. 801,441, filed May 27, 1977, now U.S. Pat. No. 4,160,648, and partially allowed application U.S. Ser. No. 917,426, filed June 19, 1978, now U.S. Pat. No. 4,233,168, which are incorporated herein by reference, fuel and the lube oil compositions containing novel hydrocarbyl poly(oxalkalene) aminocarbamate deposit-control additives are disclosed.

It has now been found that while these additives are effective for deposit control, many do not effectively inhibit corrosion of metal surfaces upon contact thereof with fuel and lube oil compositions containing them.

An object herein is to provide modified aminocarbamate compositions suitable for use as deposit-control additives and having improved corrosion characteristics towards metal surfaces of internal combustion engines when present in lube oil and fuel compositions.

2. Description of Prior Art

U.S. Pat. No. 3,996,024 discloses that salt reaction products of monocarboxylic acids of hydrocarbyl amines are useful as rust inhibitors and dispersants. U.S. Pat. No. 3,359,303 discloses that reaction products of polyalkyleneoxy alkyl 1-azieridine carboxylates are useful as curing agents for epoxy resins. The alkeneoxy chains contain a maximum of 20 alkeneoxy units. U.S. Pat. No. 3,658,882 discloses certain aryl carbamates and quaternary derivatives thereof useful as antistatic agents. Belgian Pat. No. 855,961, granted July 15, 1977 (the Belgian counterpart of U.S. application Ser. No. 801,444, filed May 27, 1977 now abandoned, and related applications) discloses compounds suitable for deposit control in fuel compositions which are hydrocarbyl-poly(oxyalkylene) aminocarbamates of ethylene diamine.

SUMMARY OF THE INVENTION

A method is provided for controlling deposition of solids and inhibiting metal corrosion in intake systems and combustion chambers of internal combustion engines by use of a fuel or lube oil additive comprising the salt of an oxyacid ester of phosphorus and a hydrocarbyl poly(oxyalkalene) aminocarbamate deposit-control compound.

Further and preferred aspects of the invention are the aforementioned salt composition and a lube and fuel oil composition containing a minor amount of the salt, wherein the salt is of the formula

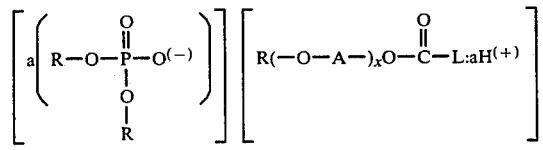

or

-continued

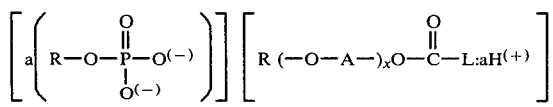

wherein:

(1) said R groups are the same or different hydrocarbyl groups having a carbon atom content in the range from 1 to 30 selected from the group consisting of phenyl, mono-, di- and trialkylphenyl, alkyl, cycloalkyl, alkenyl, cycloalkenyl, and combinations thereof;

(2) "A" is an alkylene group having a carbon atom content in the range of from 2 to 5 and x is an integer sufficient to provide said cation in unprotonated form with a molecular weight in the range of from about 500 to 10,000, (3) L is monovalent and selected from the group consisting of radicals of the formula

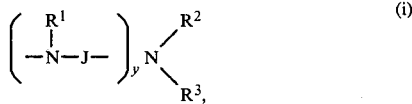

wherein J is an alkylene group having a carbon atom content in the range 2 to 6 and y is an integer in the range 1 to 11, and

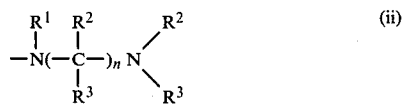

wherein n is an integer in the range 2 to 6;

(4) $R^1$, $R^2$, and $R^3$ are the same or different groups having a carbon atom content in the range 0 to 16 selected from the group consisting of hydrogen, hydrocarbyl, acyl, alkoxy, ketoalkyl, hydroxyalkyl, and cyanoalkyl groups; and (5) "a" is an integer in the range 1 to 3.

Although they are generally more costly than less complicated compounds, those wherein the group L of the above formula contains a heterocyclic amino moiety are also suitable for use herein. For example, an $R^2$ and $R^3$ group bonded to the same nitrogen atomation may form a 5 or 6-membered saturated or unsaturated nitrogen heterocyclic radical, such as pyrrolyl, pyrrolidinyl, imidazolidinyl, oxazolidinyl, pyrrolinyl, imidazolinyl, piperidino, piperazinyl, isoxazolyl, hexahydrotriazinyl, triazinyl, morpholino, etc. and these heterocyclic radicals may be substituted by hydrogen and one or two of the carbon-containing groups described in (4) above.

DETAILED DESCRIPTION OF THE INVENTION

The salts of the present invention comprise an anion portion which is a mono- or dibasic hydrocarbyl ester of an oxyacid of phosphorus and a cation portion which is a protonated hydrocarbyl poly(oxyalkylene) aminocarbamate deposit-control additive containing from 1 to 3, preferably one, protonated basic nitrogen atoms. These salts are prepared by any convenient method normally employed in reacting an acid with a high molecular weight nitrogen-containing base, for example, separately dissolving them in a suitable solvent, admixing the two solutions with moderate heating and thorough mixing of the resulting mixture. Depending upon the contemplated use of the salt, the solvent may or may not be removed, for example by evaporation under vacuum or the like.

In general oxyacid esters of phosphorus are suitable for use in preparing the salts herein, provided that they contain at least one ester or hydrocarbyl group and one or two, preferably one, hydroxyl group.

A convenient formulation of the oxyacid esters satisfactory for use herein is

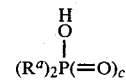

wherein said $R^a$ groups are the same or different and selected from the group consisting of hydrogen, hydroxyl and carbon-containing groups having a carbon atom content in the range 1 to 30, consisting of hydrocarbyl and hydrocarbyloxy and wherein c is an integer in the range 0 to 1 and provided that at least one $R^a$ group is OR. Preferably the acid is a phosphoric acid ester in which the $R^a$ groups are hydrocarbyloxy groups having a carbon atom content in the range 6 to 30, more preferably 6 to 20. Broadly, the hydrocarbyl groups of the acid ester are monovalent organic radicals composed essentially of hydrogen and carbon, and may be aliphatic, aromatic, or alicyclic, or a combination thereof, and may be saturated or unsaturated. Typical hydrocarbyl groups are: octyl, isooctyl, octadecyl, pentacosyl, tricontyl, propylphenyl, dodecylphenyl, pentadecylphenyl, tetracosylphenyl and tricosylbenzyl.

Typical hydrocarbyloxy (R—O—) groups of the acid esters herein include octyloxy, octadecyloxy, isooctyloxy, pentacosyloxy, tricontyloxy, propylphenyloxy, dodecylphenyloxy, pentadecylphenoxy, polypropyloxy, tetracosylphenoxy, and tricosylbenzyloxy.

Representative acid esters useful in the present invention include:

Dioctyl hydrogen phosphate
Didodecyl hydrogen phosphate
Dipentadecyl hydrogen phosphate
Octacosyl hydrogen phosphate
Tridecyl pentadecyl hydrogen phosphate
Eicosyl nonyldecyl hydrogen phosphate
Tetradecyl dihydrogen phosphate
Pentacosyl dihydrogen phosphate
Heptadecyl propyl hydrogen phosphate
Methyldodecyl hydrogen phosphate
Ethyl decyl hydrogen phosphate
Isopropyl eicosyl hydrogen phosphate
2-octaphenyl dihydrogen phosphate
4-dodecylphenyl dihydrogen phosphate
2,4-dibutylphenyl dihydrogen phosphate
4-tetradecylbenzyl dihydrogen phosphate
di(4-pentaphenyl) hydrogen phosphate
Ethylbenzene phosphonic acid
Methyl hydrogen ethylbenzene phosphonate
Tetradecyl hydrogen ethane phosphonate
Octadecyl hydrogen phosphonate
Eicosyl hydrogen phosphonate
Heptadecane phosphonic acid
4-dodecylphenyl hydrogen methane phosphonate
Octadecylphosphinic acid
Docosyl phosphinic acid
Octyl phosphinic acid
Dodecylphenyl phosphinic acid Didecyl hydrogen phosphite
Dodecylphenyl dihydrogen phosphite
Octyl benzyl hydrogen phosphite
Octadecyl dihydrogen phosphite
Hexacosyl dihydrogen phosphite
Nonyl tridecyl hydrogen phosphite
Butyl eicosyl hydrogen phosphite
Heptadecyl hydroen phosphonite
Triacontyl hydrogen phosphonite
Docosyl hydrogen phosphonite
Dodecyl hydrogen propanephosphonite
Octyl hydrogen dodecanephosphonite
Tridecylphenyl hydrogen phosphonite
Tetradecyl hydrogen benzenephosphonite
Octadecane phosphinous acid
Undecylbenzene phosphinous acid In general, hydrocarbyl poly(oxyalkene)aminocarbamates suitable for use as deposit control additives in fuels or lube oils are satisfactory for use in preparing the salts of the invention. These carbamates and their preparation are disclosed in our above-referenced applications. They consist of an amine moiety and a poly(oxyalkalene) moiety comprising at least one hydrocarbyl-terminated poly(oxyalkylene) polymer bonded through a carbamate linkage, i.e.,

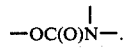
—OC(O)N—.

The amine component of the carbamate and the poly(oxyalkylene) component of the carbamate are selected to provide solubility in fuel or lube oil compositions and deposit control activity without octane requirement increase.

Amine Component

The amine moiety of the hydrocarbyl-terminated poly(oxyalkylene) aminocarbamate is preferably derived from a polyamine having from 2 to about 12 amino nitrogen atoms and from 2 to about 40 carbon atoms. The polyamine is preferably reacted with a hydrocarbylpoly(oxyalkylene) chloroformate to produce the hydrocarbylpoly(oxyalkylene) aminocarbamate fuel or lube oil additive finding use within the scope of the present invention. The chloroformate is itself derived from hydrocarbylpoly(oxyalkylene) alcohol by reaction with phosgene. The polyamine, encompassing diamines, provides the product poly(oxyalkylene) aminocarbamate with, on the average, at least about one basic nitrogen atom per carbamate molecule, i.e., a nitrogen atom titratable by a strong acid. The polyamine preferably has a carbon-ton-nitrogen ratio of from about 1:1 to about 10:1. Preferably, the amine moiety contains at least one primary or secondary amino nitrogen, e.g. has one or two attached hydrogen atoms.

Hydrocarbyl, as used in describing all the components of this invention, denotes an organic radical composed of carbon and hydrogen which may be aliphatic, alicyclic, aromatic or combinations thereof, e.g., aralkyl. Preferably, the hydrocarbyl group will be relatively free of aliphatic unsaturation, i.e., ethylenic and acetylenic, particularly acetylenic unsaturation. The substituted polyamines of the present invention are generally, but not necessarily, N-substituted polyamines. Exemplary hydrocarbyl groups and substituted hydrocarbyl groups include alkyls such as methyl, ethyl, propyl, butyl, isobutyl, pentyl, hexyl, octyl, etc., alkenyls such as propenyl, isobutenyl, hexenyl, octenyl, etc., hydroxyalkyls, such as 2-hydroxyethyl, 3-hydroxypropyl, hydroxyisopropyl, 4-hydroxybutyl, etc., ketoalkyls, such as 2-ketopropyl, 6-ketooctyl, etc., alkoxy and lower alkenoxy alkyls, such as ethoxyethyl, ethoxypropyl, propoxyethyl, propoxypropyl, 2-(2-ethoxyethoxy)ethyl, 2-(2-(2-ethoxyethoxy)ethoxy)ethyl, 3,6,9,12-tetraoxatetradecyl, 2-(2-ethoxyethoxy)hexyl, etc. Representative of the aforementioned acyl group substituents are such as propionyl, acetyl, etc. The more preferred substituents are hydrogen, $C_1$–$C_6$ alkyls and $C_1$–$C_6$ hydroxyalkyls.

In a substituted polyamine the substituents are found at any atom capable of receiving them. The substituted atoms, e.g., substituted nitrogen atoms, are generally geometrically inequivalent, and consequently the substituted amines finding use in the present invention can be mixtures of mono- and poly-substituted polyamines with substituent groups situated at equivalent and/or inequivalent atoms.

The more preferred polyamine finding use within the scope of the present invention is a polyalkylene polyamine, including alkylene diamine, and including substituted polyamines, e.g., alkyl and hydroxyalkyl-substituted polyalkylene polyamine. Preferably, the alkylene group contains from 2 to 6 carbon atoms, there being preferably from 2 to 3 carbon atoms between the nitrogen atoms. Such groups are exemplified by ethylene, 1,2-propylene, 2,2-dimethyl-propylene, trimethylene, 1,3,2-hydroxypropylene, etc. Examples of such polyamines include ethylene diamine, diethylene triamine, di(trimethylene)-triamine, dipropylene triamine, triethylene tetramine, tripropylene tetramine, tetraethylene pentamine, and pentaethylene hexamine. Such amines encompass isomers such as branched-chain polyamines and the previously mentioned substituted polyamines, including hydroxy- and hydrocarbyl-substituted polyamines. Among the polyalkylene polyamines, those containing 2–12 amine nitrogen atoms and 2–24 carbon atoms are especially preferred, and the $C_2$–$C_3$ alkylene polyamines are most preferred, in particular, the lower polyalkylene polyamines, e.g., ethylene diamine, dipropylene triamine, etc.

The amine component of the poly(oxyalkylene) aminocarbamate also may be derived from heterocyclic polyamines, heterocyclic substituted amines and substituted heterocyclic compounds, wherein the heterocycle comprises one or more 5-6-membered rings containing oxygen and/or nitrogen. Such heterocycles may be saturated or unsaturated and substituted with groups such as discussed above. The heterocycles are exemplified by piperazines, such as 2-methylpiperazine, N-(2-hydroxyethyl)piperazine, 1,2-bis-(N-piperazinyl)ethane, and N,N'-bis(N-piperazinyl)piperazine, 2-methylimidazoline, 3-aminopiperidine, 2-aminopyridine, 2-aminopyridine, 2-(3-aminoethyl)-3-pyrroline, 3-aminopyrrolidine, N-(3-aminopropyl)-morpholine, etc. Among the heterocyclic compounds, the piperazines are preferred.

Typical polyamines that can be used to form the compounds of this invention by reaction with a poly(oxyalkylene)chloroformate include the following: ethylene diamine, 1,2-propylene diamine, 1,3-propylene diamine, diethylene triamine, triethylene tetramine, hexamethylene diamine, tetraethylene pentamine, dimethylaminopropylene diamine, N-(beta-aminoethyl)piperazine, N-(beta-aminoethyl)piperidine, 3-amino-N-ethylpiperidine, N-(beta-aminoethyl)morpholine, N,N'- di(beta-aminoethyl)piperazine, N,N'-di(beta-aminoethyl)imidazolidone-2,N-(beta-cyanoethyl)ethane-1,2-diamine, 1-amino-3,6,9-triazaoctadecane, 1-amino-3,6-diaza-9-oxadecane, N-(beta-aminoethyl)-diethanolamine, N'-acetyl-N'-methyl-N-(beta-aminoethyl)ethane-1,2-diamine, N-acetonyl-1,2-propanediamine, N-(beta-nitroethyl)-1,3-propane diamine, 1,3-dimethyl-5-(betaaminoethyl)hexahydrotriazine, N-(beta-aminoethyl)hexahydrotriazine, 5-(beta-aminoethyl)-1,3,5-dioxazine, 2(2-aminoethylamino)-ethanol, 2-[2-(2-aminoethylamino)ethylamino]-ethanol.

The amine component of the poly(oxyalkylene) aminocarbamate may also be derived from an amine-containing compound which is capable of reacting with a hydrocarbylpoly(oxyalkylene) alcohol to produce a hydrocarbylpoly(oxyalkylene) aminocarbamate having at least one basic nitrogen atom. For example, a substituted aminoisocyanate, such as $(R)_2NCH_2CH_2NCO$, wherein R is, for example, a hydrocarbyl group, reacts with the alcohol to produce the aminocarbamate additive finding use within the scope of the present invention. Typical aminoisocyanates that may be used to form he fuel additive compounds of this invention by reaction with a hydrocarbylpoly(oxyalkylene) alcohol include the following: N,N-(dimethyl)aminoisocyanatoethane, generally, N,N-(dihydrocarbyl)aminoisocyanatoalkane, more generally, N-(perhydrocarbyl)isocyanatopolyalkylene polyamine, N,N-(dimethyl)aminoisocyanatobenzene, etc.

In many instances the amine used as a reactant in the production of the carbamate of the present invention is not a single compound but a mixture in which one or several compounds predominate with the average composition indicated. For example, tetraethylene pentamine prepared by the polymerization of aziridine or the reaction of dichloroethylene and ammonia will have both lower and higher amine members, e.g., triethylene tetramine, substituted piperazines and pentaethylene hexamine, but the composition will be mainly tetraethylene pentamine and the empirical formula of the total amine composition will closely approximate that of tetraethylene pentamine. Finally, in preparing the compounds of this invention, where the various nitrogen atoms of the polyamine are not geometrically equivalent, several substitutional isomers are possible and are encompassed within the final product. Methods of preparation of amines, isocyanates and their reactions are dettailed in Sidgewick's "The Organic Chemistry of Nitrogen," Clarendon Press, Oxford, 1966: Noller's "Chemistry of Organic Compounds," Saunders, Philadelphia, 2nd Ed., 1957; and Kirk-Othmer's "Encyclopedia of Chemical Technology," 2nd Ed., especially Volume 2, pp. 99–116.

Poly(oxyalkylene) Component

The hydrocarbyl-terminated poly(oxyalkylene) polymers which are utilized in preparing the carbamates of the present invention are monohydroxy compounds, i.e., alcohols, often termed monohydroxy polyethers, or polyalkylene glycol monohydrocarbylethers, or "capped" poly(oxyalkylene) glycols and are to be distinguished from the poly(oxyalkylene) glycols (diols), or polyols, which are not hydrocarbyl-terminated, i.e., not capped. The hydrocarbyl-terminated poly(oxyalkylene) alcohols are produced by the addition of lower alkylene oxides, such as oxirane, ethylene oxide, propylene oxide, the butylene oxides, or the pentylene oxides to the hydroxy compound ROH under polymerization conditions, wherein R is the hydrocarbyl group which caps the poly(oxyalkylene) chain. Methods of production and properties of these polymers are disclosed in U.S. Pat. Nos. 2,841,479 and 2,782,240, and the aforementioned Kirk-Othmer's "Encyclopedia of Chemical Technology," Volume 19, p. 507. In the polymerization reaction a single type of alkylene oxide may be employed, e.g., propylene oxide, in which case the product is a homopolymer, e.g., a poly(oxypropylene) propanol. However, copolymers are equally satisfactory and random copolymers are readily prepared by contacting the hydroxyl-containing compound with a mixture of alkylene oxides, such as a mixture of propylene and butylene oxides. Block copolymers of oxyalkylene units also provide satisfactory poly(oxyalkylene) polymers for the practice of the present invention. Random polymers are more easily prepared when the reactivities of the oxides are relatively equal. In certain cases, when ethylene oxide is copolymerized with other oxides, the higher reaction rate of ethylene oxide makes the preparation of random copolymers difficult. In either case, block copolymers can be prepared. Block copolymers are prepared by contacting the hydroxyl-containing compound with first one alkylene oxide, then the others in any order, or repetitively, under polymerization conditions. A particular block copolymer is represented by a polymer prepared by polymerizing propylene oxide on a suitable monohydroxy compound to form a poly(oxypropylene) alcohol and then polymerizing butylene oxide on the poly(oxypropylene) alcohol.

In general, the poly(oxyalkylene) polymers are mixtures of compounds that differ in polymer chain length. However, their properties closely approximate those of the polymer represented by the average composition and molecular weight.

The hydrocarbylpoly(oxyalkylene) moiety of the carbamate consists of one or more hydrocarbyl-terminated poly(oxyalkylene units containing from 2 to about 5 carbon atoms. The polymers are bound to the aminocarbamate via the oxygen atom of carbamate linkages, and the poly(oxyalkylene) moiety consists of at least one such poly(oxyalkylene) polymer. The hydrocarbyl group contains from 1 to about 30 carbon atoms, preferably from 2 to about 20 carbon atoms. Preferably the oxyalkylene units contain from 3 to 4 carbon atoms and the molecular weight of the hydrocarbyl poly(oxyalkylene) moiety is from about 500 to 10,000, more preferably from about 500 to about 5,000. Each poly(oxyalkylene) polymer contains at least about 5 oxyalkylene units, preferably 8 to about 100 oxyalkylene units, more preferably about 10–100 units and most preferably 10 to about 25 such units. In general, the oxyalkylene units may be branched or unbranched. Preferably the poly(oxyalkylene) polymer chain contains at least some $C_3$–$C_5$ oxyalkylene units, more preferably branched $C_3$–$C_5$ oxyalkylene units are present in at least sufficient number to render the hydrocarbyl-terminated poly(oxyalkylene) aminocarbamate soluble in the fuel composition of the present invention. This solubility condition is satisfied if the carbamate is soluble in hydrocarbons boiling in the gasoline range, at least to the extent of about 30–2,000 ppm by weight. A poly(oxyalkylene) polymer chain composed of branched three and/or four carbon oxyalkylene units in at least sufficient amount to effect solubility in the fuel composition is most preferred. The structures of the $C_3$–$C_5$ oxyalkylene units are many of the isomeric structures well known to the organic chemist, e.g., n-propylene, —CH₂CH₂CH₂—; isopropylene, —C(CH₃)CH₂—; n-butylene, —CH₂CH₂CH₂CH₂—; sec.-butylene, —CH(CH₂CH₃)CH₂—; tert.-butylene, —C(CH₃)₂CH₂—; disec.-butylene, —CH(CH₃)CHCH₃)—; isobutylene, —CH₂CH(CH₃)CH₂—; etc. The preferred poly(oxyalkylene) compounds are composed, at least in part, of the branched oxyalkylene isomers, particularly oxy(isopropylene), and oxy(sec.-butylene) units which aare obtained from 1,2-propylene oxide and from 1,2-butylene oxide, respectively.

The hydrocarbyl moiety (R) which terminates the poly(oxyalkylene) chain contains from 1 to about 30 carbon atoms, preferably from 2 to about 20 carbon atoms, and is generally derived from the monohydroxy compound (ROH) which is the initial site of the alkylene oxide addition in the polymerization reaction. Such monohydroxy compounds are preferably aliphatic or aromatic alcohols of from 1 to about 30 carbon atoms, more preferably an alkanol or an alkylphenol, and most preferably an alkylphenol wherein the alkyl is a straight or branched chain of from 1 to about 24 carbon atoms. One such preferred alkyl group is obtained by polymerizing propylene to an average of 4 units and has the common names of propylene tetramer. The preferred material may be termed either an alkylphenylpoly(oxyalkylene) alcohol or a polyalkoxylated alkylphenol.

Hydrocarbylpoly(oxyalkylene) Aminocarbamate

Having described the amine component and the poly(oxyalkylene) component, the poly(oxyalkylene) aminocarbamate used to prepare the salt composition of the present invention is obtained by linking these components together through a carbamate linkage, i.e.,

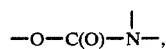

wherein the oxygen may be regarded as the terminal hydroxyl oxygen of the poly(oxyalkylene) alcohol component, and the carbonyl group, —C(O)—, is preferably provided by a coupling agent, e.g., phosgene. In the preferred method of preparation, the hydrocarbylpoly(oxyalkylene) alcohol is reacted with phosgene to produce a hydrocarbylpoly(oxyalkylene) chloroformate. The chloroformate is reacted with a polyamine. The carbamate linkages are formed as the poly(oxyalkylene) chains are bound to the nitrogen of the polyamine through the oxycarbonyl group (—O—C(O)—) of the chloroformate. Since there may be more than one nitrogen atom of the polyamine which is capable of reacting with the chloroformate, the hydrocarbylpoly(oxyalkylene) aminocarbamate contains at least one hydrocarbylpoly(oxyalkylene) polymer chain bonded through an oxycarbonyl group to a nitrogen atom of the polyamine, but the carbamate may contain from 1 to 2 or more such chains. It is preferred that the hydrocarbylpoly(oxyalkylene) aminocarbamate product contain, on the average, about 1 poly(oxyalkylene) chain per molecule (i.e., monocarbamate, although it is understood that this reaction route may lead to mixtures containing appreciable amounts of di- or higher poly(oxyalkylene) chain substitution on a polyamine containing several reactive nitrogen atoms (i.e., dicarbamate or higher degree of substitution). To avert di- or higher substitution on the polyamine, a large excess of polyamine is desirably contacted with the chloroformate.

The hydrocarbylpoly(oxyalkylene) aminocarbamate finding use within the scope of the present invention is characterized by having at least about one basic nitrogen atom per molecule. Since, within the compositional mixture, the amine moiety may contain more or less nitrogen, and consequently the poly(oxyalkylene) moiety of the carbamate may contain more than one poly(oxyalkylene) polymer, the aminocarbamate is further characterized by having, on the average, at least one basic nitrogen atom per aminocarbamate molecule. A "basic nitrogen atom" is one that is titratable by a strong acid, e.g., a primary, secondary or tertiary amino nitrogen, as distinguished from, for example, amido nitrogens,

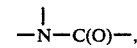

which are not so titratable or quaternary nitrogen. Preferably, at least one of the basic nitrogen atoms is in a primary or secondary amino group.

The preferred hydrocarbylpoly(oxyalkylene) aminocarbamate has a molecular weight of from about 600 to about 10,000 (representing an average maximum disubstitution of poly(oxyalkylene) polymer in the carbamate) and more preferably from about 1,200 to about 5,000.

Preparation of the Poly(oxyalkylene) Amino Carbamates

The poly(oxyalkylene) aminocarbamates suitable for use herein may be most conveniently prepared, as has been previously noted, by reaction of phosgene with the monohydroxy poly(oxyalkylene) compound followed by reaction of the product with a suitable amine.

Bis(aminocarbamates), which we have made by reacting phosgene with an "uncapped" poly(oxyalkylene) diol followed by reaction with polyamine, have been found to have no deposit control activity; in fact, they may contribute significantly to valve deposits.

The reaction of the poly(oxyalkylene) compound and phosgene is usually carried out on an essentially equimolar basis, although excess phosgene can be used to improve the degree of reaction. Of course, excess phosgene is stripped from the product chloroformate before reaction with polyamine. The reaction may be carried out at temperatures from −10° to 100° C., preferably in the range of 0° to 50° C. The reaction will usually be complete within ¼ to 5 hours. Times of reaction will usually be in the range of from 2 to 4 hours.

A solvent may be used in the chloroformylation reaction. Suitable solvents include benzene, toluene, etc.

The reaction of the resultant chloroformate with the amine may be carried out neat or preferably in solution. Temperatures of from −10° to 200° C. may be utilized. The desired product may be obtained by water wash and stripping, usually by the aid of vacuum, of any residual solvent.

The mol ratio of the basic amine nitrogen to polyether chloroformate will generally be in the range from about 2 to 20 mols of basic amine nitrogen per mol of choroformate, and more usually 5 to 15 mols of basic amine nitrogen per mol of chloroformate. The mol ratio will depend upon the particular amine and the desired ratio of polyether to amine. Since suppression of polysubstitution of the alkylene polyamines is usually desired, large mol excesses of the amine will be used. For example, preparation of the aminocarbamate from ethylenediamine with an ethylenediamine to chloroformate mol ratio of 2.5 to 1 has yielded a basic nitrogen to total nitrogen ratio in the product of 0.27, whereas raising the basic amine nitrogen to chloroformate ratio to 9.1 to 1 gives 0.42 basic nitrogen to total nitrogen ratio, showing a much higher amount of monocarbamate in the material.

The reaction or reactions may be conducted with or without the presence of a reaction solvent. A reaction solvent is generally employed whenever necessary to reduce the viscosity of the reaction product. These solents should be stable and inert to the reactants and reaction product. Preferred solvents include aliphatic or aromatic hydrocarbons or aliphatic alcohols. Depending on the temperature of the reaction, the particular chloroformate used, the mol ratios and the particular amine, as well as the reactant concentrations, the reaction time may vary from less than 1 minute to 3 hours.

After the reaction has been carried out for a sufficient length of time, the reaction mixture may be subjected to extraction with a hydrocarbon-water or hydrocarbon-alcohol-water medium to free the product from any low-molecular-weight amine salts which have formed and any unreacted alkylene polyamines. The product may then be isolated by evaporation of the solvent. Small amounts of halogen may be present as the hydrohalide salt of the polyether aminocarbamates.

Although the amino carbamates required for preparation of the salts of the present invention have been described in terms of amine and poly(oxyalkylene) components coupled via a chloroformylation reaction utilizing phosgene, as is known to those of skill in the art, there are other methods of preparing carbamates which use other reactants. For example, the reaction of an isocyanate with an alcohol such as the hydroxycarbyl-poly(oxyalkylene) alcohol described above also produces a carbamate. Monoisocyanato amines are produced, for example, by the methods of U.S. Pat. No. 3,644,490. Consequently, it is, for example, within the skill of the art to use a selected isocyanate-substituted amine or polyamine to react directly with said poly(oxyalkylene) alcohol to produce a carbamate within the scope of the present invention. This route may be exemplified by the reaction of $(CH_3)_2NCH_2CH_2N\!=\!C\!=\!O$ with a hydrocarbylpoly(oxyalkylene) alcohol to produce a carbamate characteristic of the present invention. Another method for the preparation of the carbamates required herein is via a displacement reaction on a polyether carbonate with a polyamine.

Salt Compositions

The salts of the present invention are produced by efficiently admixing one or more of the above-described oxyacid esters of phosphorus with one or more of the above-described hydrocarbyl poly(oxyalkylene) carbamates. These salts should be neutral or basic, that is contain no unneutralized acid, for example as would be the case of the salt obtained by reacting one mol of a carbamate herein containing a single basic nitrogen atom with one mol of a dihydrogen phosphate ester. Preferred salts of the invention are of the formula

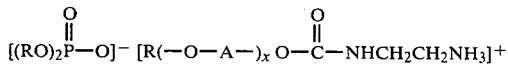

wherein R is the same or different and a hydrocarbyl group having a carbon atom content in the range 6 to 20 and selected from the group consisting of alkyl, mono- and dialkylphenyl, phenylalkyl and cycloalkyl groups and said groups containing a single carbon-carbon double bond; wherein A and x are as defined in the prior salt formula above.

In order to prepare the sale of the present invention, the acid ester and hydrocarbyl poly(oxyalkylene) carbamate are combined in a suitable medium in appropriate proportions based upon the equivalent weights thereof (see for example U.S. Pat. No. 3,996,024, Marvin D. Coon.) Useful media include alcohols, mixtures of alcohols, hydrocarbons, etc. such as t-butyl alcohol, toluene, and xylene. By a suitable choice of solvent, the product may be obtained directly as a concentrate for use in combining with fuels or lube oils. Equivalent weights of the acid esters and carbamates may be determined by conventional means, for example by potentiometric titrations, prior to mixing to facilitate admixing of substantially equivalent amounts of the reactants.

Fuel Compositions

The salts of the invention will generally be employed in a hydrocarbon distillate fuel or lube oil. Where used as a fuel additive, the proper concentration of additive necessary in order to achieve the desired detergency, dispersancy and corrosion resistance varies depending upon the type of fuel employed, the presence of other detergents, dispersants and other additives, etc. Generally, however, from 30 to 2000 weight parts per million, preferably from 50 to 250 ppm of salt per part of base fuel is needed to achieve the best results. When other detergents are present, a lesser amount of salt may be used. For example, the salt of the aminocarbamate may be used with an additional amount of unneutralized aminocarbamate to provide optimum dispersancy and corrosion properties. For performance as a carburetor detergent and corrosion inhibitor, lower concentrations, for example 30 to 70 parts per million may be preferred.

The salt may be formulated as a concentrate, using a inert stable oleophilic organic solvent boiling in the range of about 65° to 200° C. Preferably, an aliphatic or an aromatic hydrocarbon solvent is used, such as benzene, toluene, xylene or higher-boiling aromatics or aromatic thinners. Aliphatic alcohols of about 3 to 8 carbon atoms, such as isopropanol, isobutylcarbinol, n-butanol and the like, in combination with hydrocarbon solvents are also suitable for use with the detergent-dispersant additive. In the concentrate, the amount of the additive will be ordinarily at least 10 percent by weight and generally not exceed 70 percent by weight, preferably 10–50 weight percent and most preferably from 10 to 25 weight percent.

In gasoline fuels, other fuel additives may also be included such as antiknock agents, e.g., methylcyclopentadienyl manganese tricarbonyl, tetramethyl or tetraethyl lead, or other dispersants or detergents such as various substituted succinimides, amines, aminocarbamates, etc. Also included may be lead scavengers such as aryl halides, e.g., dichlorobenzene or alkyl halides, e.g., ethylene dibromide. Additionally, antioxidants, metal deactivators and demulsifiers may be present.

A particularly useful additive is a fuel-soluble carrier oil. Exemplary carrier oils include nonvolatile poly(oxyalkylene) alcohols, diols (glycols) and polyols used singly or in mixtures, such as the Pluronics marketed by BASF Wyandotte Corp., and the UCON LB-series fluids marketed by Union Carbide Corp. When used, these carrier oils are believed to act as a carrier for the detergent and assist in removing and retarding deposits. They have been found to display synergistic effects when combined with certain hydrocarboxypoly(oxyalkylene) aminocarbamates. They are employed in amounts from about 0.005 to 0.5 percent by volume, based on the final gasoline composition. Preferably 100–5000 ppm by weight of a fuel soluble poly(oxyalkylene) alcohol, glycol or polyol is used as carrier oil. In the previously described concentrate the poly(oxyalkylene) alcohol, diols (glycols) and polyols are usually present in amounts of from 5 to 80 percent by weight. A particularly preferred poly(oxyalkylene) carrier oil is poly(oxyalkylene) alcohol, glycol or polyol, especially the alcohol, e.g., a ($C_1$–$C_{10}$ hydrocarbyl)poly(oxypropylene) alcohol.

Lube Oil Compositions

The salts of the present invention are useful additives for lube oil compositions for lubricating internal combustion engines. The salts herein, because of their deposit control and corrosion inhibitory characteristics, help maintain a high degree of cleanliness of lubricated parts and a reduction in corrosion of metal surfaces. They also find special utility in synthetic (polyether) base stocks.

Suitable lubricating oils which can be used to prepare a lubricating oil composition or concentrate of this invention are oils of lubricating viscosity derived from petroleum or synthetic sources. The oils can be paraffinic, naphthenic, halo-substituted hydrocarbons, synthetic esters, polyethers, alkylbenzenes, or combinations thereof. Oils of lubricating viscosity have viscosities in the range of 35 to 50,000 SUS at 100° F., and more usually from about 50 to 10,000 SUS at 100° F. The amount of the salt of this invention which is incorporated into the lubricating oil to provide the effective amount necessary for dispersancy varies widely with the particular salt used as well as the use intended for the lubricating oil composition. Other conventional additives which can be used in combination with the salts of this invention include ashless dispersants such as the type disclosed in U.S. Pat. Nos. 3,172,892, 3,219,666, 3,381,022; neutral and basic calcium, barium and magnesium petrosulfonates or alkyl phenates; oxidation inhibitors, antifoam agents, viscosity index improvers, pour-point depressants, and the like, such as chlorinated wax, benzyldisulfide, sulfurized sperm oil, sulfurized terpene; phosphorus esters such as trihydrocarbon phosphites and phosphates; metal thiocarbamates such as zinc dioctyldithiocarbamate; metal phosphorus dithioates such as zinc dioctylphosphorodithicate; polyisobutene having an average molecular weight of 100,000; etc.

In general, the lubricating oil compositions will contain from about 0.01 to about 20 weight percent of the salt. More usually, the lubricating oil composition of the invention will contai from about 0.5 to about 10 weight percent of the salt and more usually from about 1 to about 8 weight percent thereof.

In a further embodiment of this invention, lubricating oil additive concentrates are provided comprising from about 90 to about 20 weight percent of an inert stable oleophilic solvent such as oil of lubricating viscosity and from about 10 to about 80 weight percent of the poly(oxyalkylene) aminocarbamates of this invention. Typically, the concentrates contain sufficient diluent to make them easy to handle during shipping and storage. Preferably, the diluent is an oil of lubricating viscosity so that the concentrate may be readily mixed with lubricating oils to prepare lubricating oil compositions. Suitable lubricating oils which can be used as diluents typically have viscosities in the range from about 35 to about 1000 Saybolt Universal Seconds (SUS) at 100° F., although any oil of lubricating viscosity can be used.

EXEMPLIFICATION

The following examples are presented to illustrate specific embodiments of the practice of this invention and should not be construed as limitations upon the scope of the invention.

Example 1—Preparation of Alkylphenylpoly(oxybutylene) Alcohol

The experiment was carried out in dry glassware under an inert atmosphere. Potassium (1.17 g, 0.03 mol) was added to 26.34 g (0.1 mol) of a phenol alkylated with propylene tetramer. The mixture was stirred and heated to 50° C. for 24 hours until the potassium dissolved. The pot temperature was raised to 80° C. and 1,2-epoxybutane (215 ml, 2.5 mols) was added at a rate slow enough to prevent flooding of the condenser. The reaction was stirred and heated at reflux until the pot temperature reached 125° C. The product was extracted into 2 volumes of diethyl ether and washed with two volumes of 0.5 N HCl. Diethyl ether (250 ml) was added to the ethereal layer, and it was washed four times with 250-ml aliquots of water. The solvent was removed and the product was aceotroped with toluene to remove traces of water. A yield of 145 g of a viscous liquid of molecular weight approximately 1500 was obtained.

Example 2—Reaction of Alkylphenylpoly(oxybutylene) Alcohol with Phosgene

Phosgene (14 ml, 0.198 mol) was condensed and transferred to a flask containing 150 ml of toluene. This mixture was cooled and stirred in an ice bath while the poly(oxybutylene) alcohol of Example 1 (140 g, 0.09 mol) was added dropwise. After the addition was complete, the ice bath was removed and the mixture was stirred for about 1 hour. An aliquot was taken, and the infra-red spectrum of its non-volatile residue showed a strong chloroformate absorption at 1785 $cm^{-1}$.

Example 3—Reaction of Alkylphenylpoly(oxybutylene) Chloroformate with Amine

Ethylenediamine (41 ml, 0.61 mol) was stirred rapidly and cooled in an ice bath. The chloroformate of Example 2 was diluted with four volumes of toluene and added to the ethylenediamine at such a rate that the pot temperature did not exceed 30° C. After the addition was completed, the ice bath was removed and the mixture was stirred for about 1 hour.

The mixture was extracted into 500-ml of hot n-butanol and washed four times with 500-ml aliquots of hot water. The solvent was removed and the product was azeotroped with toluene to remove traces of water, giving 125 g of a viscous amber liquid of molecular weight about 1600. The product alkylphenylpoly(oxybutylene)ethylenediamine carbamate, i.e., alkylphenylpoly(oxybutylene)-N-(2-aminoethyl) carbamate, contained 1.20% by weight nitrogen and dispersed sludge at 200–400 ppm.

Example 4—Reaction of Carbamate with Diisooctyl Hydrogen Phosphate

Alkylphenylpoly(oxybutylene)ethylenediamine carbamate in about a 50 weight percent solution in a heavy aromatic (mainly $C_9$-aromatics) was heated to about 60° C. To this heated solution was added a second approximately 50 weight percent solution of diisooctyl hydrogen phosphate in xylene solvent in an amount sufficient to provide in the resulting mixture an acid to basic amine equivalent ratio of 0.8 to 1. The resulting mixture was heated and maintained at about 60° C. for about one-half hour. A salt concentrate was then produced by stripping the lower boiling fraction of the solvent from the reaction mixture.

Example 5—Dispersancy Test

The polypropylphenyl poly(oxybutylene) ethylenediamine carbamate diisooctyl phosphate salt prepared in Example 4 was tested for dispersancy in a laboratory test. In this test, the hexane-insoluble, chloroform-soluble fraction of sludge scraped from the crankcase of high mileage engines is used. This fraction in the form of a 2.7 weight percent chloroform solution is added to a typical base gasoline containing varying amounts of the test additive. The concentration of salt additive required to prevent coagulation and precipitation of the sludge for a period of at least 30 minutes was measured. A comparison of the amounts (ppmw) required in this test for the carbamate itself and the salt was as follows:

| The carbamate | 200–400 |
|---|---|
| The carbamate salt | 400–800 |

These data demonstrate that the salt is a good dispersant yet not quite as effective as the carbamate.

Example 6—ASTM D1094 Interface and Phase Separation Rating Test

This test is a qualitative determination of the effect of the additive on the water-fuel interface and phase separation effects under test conditions of a fuel containing the additive. A sample of the fuel is shaken, using standardized technique, at room temperature with a phosphate buffer solution. The interface condition is rated on a basis of 1 to 4 with 1 being excellent and 4 poor. A comparison in this test of the interface ratings for the carbamate itself and the salt when present in 200 ppmw in a typical base gasoline was as follows:

| The carbamate | 3 |
|---|---|
| The carbamate salt | 1 |

These data demonstrate that the salt of the present invention exhibits relative to the carbamate additive, markedly superior water-fuel interface characteristics.

A comparison of the phase separation results (3a=- water on walls of cylinder in fuel phase; 3b=emulsion in water phase; and 2=fuel haze . . . very slight) was as follows:

| The carbamate | 3a |
|---|---|
| The carbamate salt | 1 |

These data also demonstrate that the salt of the present invention exhibits, relative to the carbamate additive, markedly superior phase separation characteristics.

Example 7—ASTM D665 Rust Prevention Test

This test is a determination of the ability of a fuel or oil containing an additive to prevent rusting of a standard steel specimen under standard conditions, for example, contact with a stirred mixture of water and the fuel or oil tested at a temperature of 38° C. for a period of five hours. In this test tap water and 200 ppmw of the addtitive in a typical base gasoline were used. The rating was by the NACE scale of A to E as follows where
A—no rust
B++=less than 3 spots
C=approximately 5% of surface rusted
D=greater than 5% rusted
E=100% rusted
A comparison in this test of the rust prevention characteristics of the carbamate and the salt was as follows:

| The carbamate | C |
|---|---|
| The carbamate salt | B++ |

These data demonstrate that, relative to the carbamate the salt of the present invention exhibits markedly superior rust preventing characteristics.

What is claimed is:

1. An additive composition effective as a minor component in a fuel composition for reducing the deposition of solids in the intake system and inhibiting the corrosion of metal surfaces of an internal combustion engine, said additive composition comprising at least one salt of an oxyacid ester of phosphorus and a hydrocarbyl poly(oxyalkylene)aminocarbamate.

2. An additive composition effective as a minor component in a fuel or lubricating oil composition for reducing the deposition of solids and inhibiting corrosion in the intake system and crankcase of an internal combustion engine, said additive composition comprising at least one salt of the formula

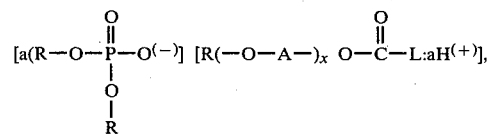

or

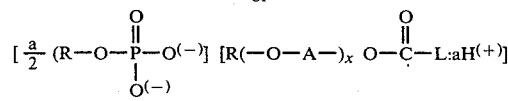

wherein:
(1) said R groups are the same or different hydrocarbyl groups having a carbon atom content in the range from 1 to 30 selected from the group consisting of phenyl, mono-, di- and trialkylphenyl, alkyl, cycloalkyl, alkenyl, cycloalkenyl, and combinations thereof;
(2) A is an alkylene group having a carbon atom content in the range of from 2 to 5 and x is an integer sufficient to provide said cation in unprotonated form with a molecular weight in the range of from about 500 to 10,000;

(3) L is monovalent and selected from the group consisting of radicals of the formula

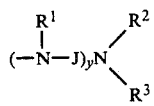 (i)

wherein J is an alkylene group having a carbon atom content in the range 2 to 6 and y is an integer in the range 1 to 11, and

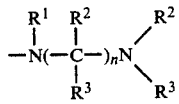

wherein n is an integer in the range 2 to 6;

(4) $R^1$, $R^2$ and $R^3$ are the same or different groups having a carbon atom content in the range 0 to 16 selected from the group consisting of hydrogen and hydrocarbyl groups selected from the group consisting of acyl, alkoxy, ketoalkyl, hydroxyalkyl and cyanoalkyl groups; and (5) a is an integer in the range 1 to 3.

3. The additive composition according to claim 2 wherein said formula is

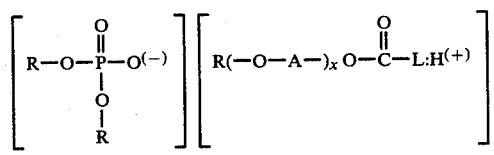

wherein R of said anion is alkyl, R of said cation is alkylphenyl and L is $NH-CH_2CH_2NH_2$.

4. The additive composition according to claim 2 wherein said additive is of the formula

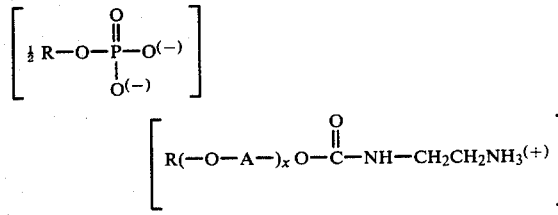

wherein R of said anion is alkyl and R of said cation is alkylphenyl.

5. A lubricating oil composition comprising a major amount of an oil of lubricating viscosity and a minor amount of at least one salt of the additive of the formula as in claim 2.

6. The composition according to claim 5 wherein said salt is of the formula

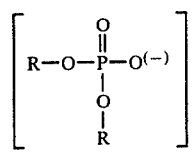

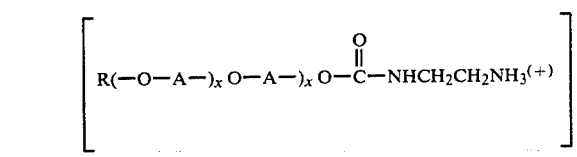

wherein R of said anion is alkyl and R of said cation is alkylphenyl.

7. A fuel composition comprising a major portion of hydrocarbon boiling in the gasoline range and an effective amount of at least one salt of the additive composition of the formula as in claim 2.

8. The composition according to claim 7 wherein said salt is of the formula

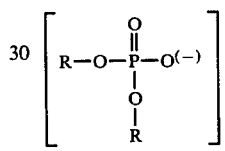

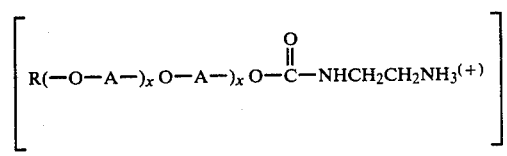

wherein R of said anion is alkyl and R of said cation is alkylphenyl.

9. The composition according to claim 7 wherein said additive is present in a fuel composition in an amount of from about 30 to 2000 ppm.

10. The composition according to claim 5 wherein said additive is present in a lubricating oil composition in an amount of from about 0.01 to about 20 weight percent.

11. A fuel or lubricating oil additive concentrate composition for use as a corrosion and solids inhibitor, said additive concentrate composition comprising an inert stable oleophilic solvent and from 10 to 80 percent by weight of at least one salt of an oxyacid ester of phosphorus and a hydrocarbyl poly(oxyalkylene)aminocarbamate.

* * * * *

UNITED STATES PATENT AND TRADEMARK OFFICE
CERTIFICATE OF CORRECTION

PATENT NO. : 4,289,634
DATED : September 15, 1981
INVENTOR(S) : Robert A. Lewis et al It is certified that error appears in the above-identified patent and that said Letters Patent are hereby corrected as shown below:

Column 18, line 15, the formula

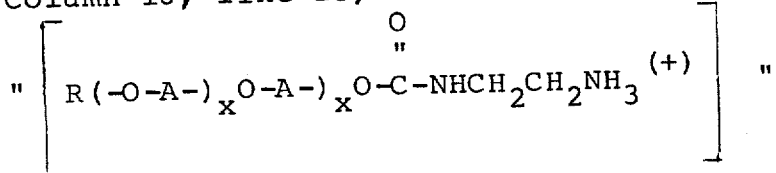

should read

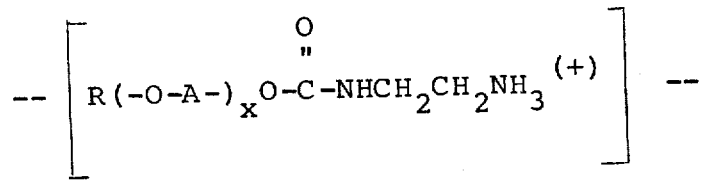

Column 18, line 35, same as above.

Signed and Sealed this

Twenty-second Day of December 1981

[SEAL]

Attest:

GERALD J. MOSSINGHOFF

Attesting Officer

Commissioner of Patents and Trademarks